(12) United States Patent
Roschin et al.

(10) Patent No.: US 11,654,001 B2
(45) Date of Patent: May 23, 2023

(54) MOLAR TRIMMING PREDICTION AND VALIDATION USING MACHINE LEARNING

(71) Applicant: ALIGN TECHNOLOGY, INC., San Jose, CA (US)

(72) Inventors: Roman A. Roschin, Moscow (RU); Evgenii Vladimirovich Karnygin, Moscow (RU); Sergey Grebenkin, Moscow (RU); Dmitry Guskov, Moscow (RU); Dmitrii Ischeykin, Moscow (RU); Ivan Potapenko, Berdsk (RU); Denis Durdin, Novosibirsk (RU); Roman Gudchenko, Moscow (RU); Vasily Paraketsov, Moscow (RU); Mikhail Gorodilov, Novosibirsk (RU); Alexey Vladykin, Balashikha (RU); Roman Solovyev, Novosibirsk (RU); Alexander Beliaev, Moscow (RU); Elizaveta Ulianenko, Novosibirsk (RU); Leonid Trofimov, Novosibirsk (RU); Anzhelika Son, Novosibirsk (RU); Nikolay Zhirnov, Moscow (RU); Alexander Vovchenko, Moscow (RU)

(73) Assignee: Align Technology, Inc., San Jose, CA (US)

( * ) Notice: Subject to any disclaimer, the term of this patent is extended or adjusted under 35 U.S.C. 154(b) by 570 days.

(21) Appl. No.: 16/593,690

(22) Filed: Oct. 4, 2019

(65) Prior Publication Data
US 2020/0107915 A1 Apr. 9, 2020

Related U.S. Application Data

(60) Provisional application No. 62/741,465, filed on Oct. 4, 2018.

(51) Int. Cl.
*A61C 9/00* (2006.01)
*A61C 13/34* (2006.01)

(52) U.S. Cl.
CPC ............ *A61C 9/0053* (2013.01); *A61C 13/34* (2013.01)

(58) Field of Classification Search
CPC .............................. A61C 13/34; A61C 9/0053
See application file for complete search history.

(56) References Cited

U.S. PATENT DOCUMENTS 5,975,893 A 11/1999 Chishti et al.
6,227,850 B1 5/2001 Chishti et al.
(Continued)

FOREIGN PATENT DOCUMENTS

EP 2389892 A1 * 11/2011 ......... A61C 13/0004
WO WO 2007/084768 A1 * 7/2007 ............. G06T 17/00
WO WO-2014060595 A1 * 4/2014 ......... A61C 13/0004

OTHER PUBLICATIONS

Zhang et al. "Efficient 3D dental identification via signed feature histogram and learning keypoint detection" Pattern Recognition 60 (2016) pp. 189-204.*

(Continued)

*Primary Examiner* — Mia M Thomas
(74) *Attorney, Agent, or Firm* — Shay Glenn LLP

(57) ABSTRACT

Provided herein are systems and methods for determining if a 3D tooth model requires trimming or removal of incomplete or missing data (e.g., gingiva covering a portion of a tooth such as a molar). A patient's dentition may be scanned and/or segmented. Raw dental features, principal component analysis (PCA) features, and/or other features may be extracted and compared to those of other teeth, such as those obtained through automated machine learning systems. A classifier can identify and/or output probability that the 3D (Continued)

tooth model requires trimming. Trimming of the 3D tooth model can be implemented without human intervention.

18 Claims, 14 Drawing Sheets

(56) References Cited

U.S. PATENT DOCUMENTS

| | | |
|---|---|---|
| 6,227,851 B1 | 5/2001 | Chishti et al. |
| 6,299,440 B1 | 10/2001 | Phan et al. |
| 6,318,994 B1 | 11/2001 | Chishti et al. |
| 6,371,761 B1 | 4/2002 | Cheang et al. |
| 6,386,878 B1 | 5/2002 | Pavlovskaia et al. |
| 6,406,292 B1 | 6/2002 | Chishti et al. |
| 6,409,504 B1 | 6/2002 | Jones et al. |
| 6,457,972 B1 | 10/2002 | Chishti et al. |
| 6,488,499 B1 | 12/2002 | Miller |
| 6,514,074 B1 | 2/2003 | Chishti et al. |
| 6,554,611 B2 | 4/2003 | Chishti et al. |
| 6,582,229 B1 | 6/2003 | Miller et al. |
| 6,602,070 B2 | 8/2003 | Miller et al. |
| 6,621,491 B1 | 9/2003 | Baumrind et al. |
| 6,688,886 B2 | 2/2004 | Hughes et al. |
| 6,726,478 B1 | 4/2004 | Isiderio et al. |
| 6,729,876 B2 | 5/2004 | Chishti et al. |
| 6,739,869 B1 | 5/2004 | Taub et al. |
| 6,767,208 B2 | 7/2004 | Kaza |
| 6,783,360 B2 | 8/2004 | Chishti |
| 7,040,896 B2 | 5/2006 | Pavlovskaia et al. |
| 7,063,532 B1 | 6/2006 | Jones et al. |
| 7,074,038 B1 | 7/2006 | Miller |
| 7,074,039 B2 | 7/2006 | Kopelman et al. |
| 7,077,647 B2 | 7/2006 | Choi et al. |
| 7,108,508 B2 | 9/2006 | Hedge et al. |
| 7,134,874 B2 | 11/2006 | Chishti et al. |
| 7,156,661 B2 | 1/2007 | Choi et al. |
| 7,160,107 B2 | 1/2007 | Kopelman et al. |
| 7,241,142 B2 | 7/2007 | Abolfathi et al. |
| 7,293,988 B2 | 11/2007 | Wen |
| 7,309,230 B2 | 12/2007 | Wen |
| 7,357,634 B2 | 4/2008 | Knopp |
| 7,555,403 B2 | 6/2009 | Kopelman et al. |
| 7,637,740 B2 | 12/2009 | Knopp |
| 7,689,398 B2 | 3/2010 | Cheng et al. |
| 7,736,147 B2 | 6/2010 | Kaza et al. |
| 7,746,339 B2 | 6/2010 | Matov et al. |
| 7,844,356 B2 | 11/2010 | Matov et al. |
| 7,844,429 B2 | 11/2010 | Matov et al. |
| 7,865,259 B2 | 1/2011 | Kuo et al. |
| 7,878,804 B2 | 2/2011 | Korytov et al. |
| 7,880,751 B2 | 2/2011 | Kuo et al. |
| 7,904,308 B2 | 3/2011 | Arnone et al. |
| 7,930,189 B2 | 4/2011 | Kuo |
| 7,942,672 B2 | 5/2011 | Kuo |
| 7,970,627 B2 | 6/2011 | Kuo et al. |
| 7,970,628 B2 | 6/2011 | Kuo et al. |
| 8,038,444 B2 | 10/2011 | Kitching et al. |
| 8,043,091 B2 * | 10/2011 | Schmitt .............. A61C 13/0004 |
| | | 433/213 |
| 8,044,954 B2 | 10/2011 | Kitching et al. |
| 8,075,306 B2 | 12/2011 | Kitching et al. |
| 8,092,215 B2 | 1/2012 | Stone-Collonge et al. |
| 8,099,268 B2 | 1/2012 | Kitching et al. |
| 8,108,189 B2 | 1/2012 | Chelnokov et al. |
| 8,126,726 B2 | 2/2012 | Matov et al. |
| 8,260,591 B2 | 9/2012 | Kass et al. |
| 8,275,180 B2 | 9/2012 | Kuo |
| 8,401,826 B2 | 3/2013 | Cheng et al. |
| 8,439,672 B2 | 5/2013 | Matov et al. |
| 8,562,338 B2 | 10/2013 | Kitching et al. |
| 8,591,225 B2 | 11/2013 | Wu et al. |
| 8,788,285 B2 | 7/2014 | Kuo |
| 8,843,381 B2 | 9/2014 | Kuo et al. |
| 8,874,452 B2 | 10/2014 | Kuo |
| 8,896,592 B2 | 11/2014 | Boltunov et al. |
| 8,930,219 B2 | 1/2015 | Trosien et al. |
| 9,037,439 B2 | 5/2015 | Kuo et al. |
| 9,060,829 B2 | 6/2015 | Sterental et al. |
| 9,125,709 B2 | 9/2015 | Matty |
| 9,211,166 B2 | 12/2015 | Kuo et al. |
| 9,220,580 B2 | 12/2015 | Borovinskih et al. |
| 9,364,296 B2 | 6/2016 | Kuo |
| 9,375,300 B2 | 6/2016 | Matov et al. |
| 9,414,897 B2 | 8/2016 | Wu et al. |
| 9,492,245 B2 | 11/2016 | Sherwood et al. |
| 9,642,678 B2 | 5/2017 | Kuo |
| 10,248,883 B2 | 4/2019 | Borovinskih et al. |
| 10,342,638 B2 | 7/2019 | Kitching et al. |
| 10,463,451 B2 * | 11/2019 | Janzadeh ............... A61C 13/34 |
| 10,463,452 B2 | 11/2019 | Matov et al. |
| 10,595,966 B2 | 3/2020 | Carrier, Jr. et al. |
| 10,617,489 B2 | 4/2020 | Grove et al. |
| 10,722,328 B2 | 7/2020 | Velazquez et al. |
| 10,758,322 B2 | 9/2020 | Pokotilov et al. |
| 10,779,718 B2 | 9/2020 | Meyer et al. |
| 10,792,127 B2 | 10/2020 | Kopelman et al. |
| 10,828,130 B2 | 11/2020 | Pokotilov et al. |
| 10,835,349 B2 | 11/2020 | Cramer et al. |
| 10,973,611 B2 | 4/2021 | Pokotilov et al. |
| 10,980,618 B2 * | 4/2021 | Schulter .................. A61K 6/20 |
| 10,996,813 B2 | 5/2021 | Makarenkova et al. |
| 10,997,727 B2 | 5/2021 | Xue et al. |
| 11,007,035 B2 * | 5/2021 | Fares ................. A61C 13/0006 |
| 11,020,205 B2 | 6/2021 | Li et al. |
| 11,020,206 B2 | 6/2021 | Shi et al. |
| 11,026,766 B2 | 6/2021 | Chekh et al. |
| 11,033,359 B2 | 6/2021 | Velazquez et al. |
| 11,071,608 B2 | 7/2021 | Derakhshan et al. |
| 11,096,763 B2 | 8/2021 | Akopov et al. |
| 11,116,568 B2 * | 9/2021 | Katzberg ............. A61B 8/0875 |
| 11,116,605 B2 | 9/2021 | Nyukhtikov et al. |
| 11,147,652 B2 | 10/2021 | Mason et al. |
| 11,151,753 B2 | 10/2021 | Gao et al. |
| 11,266,486 B2 * | 3/2022 | Balshi ................ A61C 13/0004 |
| 11,432,907 B2 * | 9/2022 | Kuo ........................ A61C 7/002 |
| 11,432,908 B2 * | 9/2022 | Kopelman ............. A61C 19/04 |
| 11,449,191 B2 * | 9/2022 | Makarenkova ..... G06F 3/04845 |
| 2003/0008259 A1 | 1/2003 | Kuo et al. |
| 2003/0143509 A1 | 7/2003 | Kopelman et al. |
| 2003/0207227 A1 | 11/2003 | Abolfathi |
| 2004/0137400 A1 | 7/2004 | Chishti et al. |
| 2004/0152036 A1 | 8/2004 | Abolfathi |
| 2004/0197728 A1 | 10/2004 | Abolfathi et al. |
| 2004/0259049 A1 | 12/2004 | Kopelman et al. |
| 2005/0182654 A1 | 8/2005 | Abolfathi et al. |
| 2005/0244791 A1 | 11/2005 | Davis et al. |
| 2006/0127836 A1 | 6/2006 | Wen |
| 2006/0127852 A1 | 6/2006 | Wen |
| 2006/0127854 A1 | 6/2006 | Wen |
| 2006/0275731 A1 | 12/2006 | Wen et al. |
| 2006/0275736 A1 | 12/2006 | Wen et al. |
| 2008/0057461 A1 * | 3/2008 | Cheng ...................... A61C 7/00 |
| | | 433/24 |
| 2008/0306724 A1 | 12/2008 | Kitching et al. |
| 2010/0009308 A1 | 1/2010 | Wen et al. |
| 2010/0068672 A1 | 3/2010 | Arjomand et al. |
| 2010/0068676 A1 | 3/2010 | Mason et al. |
| 2010/0092907 A1 | 4/2010 | Knopp |
| 2010/0167243 A1 | 7/2010 | Spiridonov et al. |
| 2013/0204599 A1 | 8/2013 | Matov et al. |
| 2016/0166362 A1 * | 6/2016 | Nonboe ............ A61C 13/0004 |
| | | 703/1 |
| 2016/0242870 A1 | 8/2016 | Matov et al. |
| 2016/0310235 A1 | 10/2016 | Derakhshan et al. |
| 2017/0273760 A1 | 9/2017 | Morton et al. |
| 2018/0035606 A1 * | 2/2018 | Burdoucci ....... H04N 5/232935 |
| 2018/0280118 A1 | 10/2018 | Cramer |
| 2019/0029784 A1 | 1/2019 | Moalem et al. |
| 2019/0053876 A1 | 2/2019 | Sterental et al. |
| 2019/0090999 A1 * | 3/2019 | Vetter .................. A61C 17/221 |
| 2019/0102880 A1 * | 4/2019 | Parpara ................... G06T 17/10 |
| 2019/0180443 A1 * | 6/2019 | Xue ....................... G06K 9/6274 |
| 2019/0192259 A1 | 6/2019 | Kopelman et al. |
| 2019/0328487 A1 | 10/2019 | Levin et al. |

(56) References Cited

U.S. PATENT DOCUMENTS

| | | | |
|---|---|---|---|
| 2019/0328488 A1 | 10/2019 | Levin et al. | |
| 2019/0333622 A1 | 10/2019 | Levin et al. | |
| 2019/0343601 A1 | 11/2019 | Roschin et al. | |
| 2020/0000552 A1* | 1/2020 | Mednikov | A61C 5/20 |
| 2020/0000554 A1* | 1/2020 | Makarenkova | A61B 5/1076 |
| 2020/0000555 A1* | 1/2020 | Yuryev | G06T 17/10 |
| 2020/0085546 A1* | 3/2020 | Li | A61C 13/20 |
| 2020/0107915 A1* | 4/2020 | Roschin | A61C 13/34 |
| 2020/0155274 A1* | 5/2020 | Pimenov | A61C 7/002 |
| 2020/0214800 A1* | 7/2020 | Matov | G06T 19/20 |
| 2020/0297458 A1* | 9/2020 | Roschin | G06F 40/10 |
| 2020/0306011 A1* | 10/2020 | Chekhonin | G16H 50/50 |
| 2020/0306012 A1* | 10/2020 | Roschin | G06F 30/10 |
| 2020/0315744 A1* | 10/2020 | Cramer | A61C 9/0053 |
| 2020/0360109 A1* | 11/2020 | Gao | G06T 7/0012 |
| 2021/0073998 A1* | 3/2021 | Brown | G16H 30/40 |
| 2021/0134436 A1* | 5/2021 | Meyer | G16H 30/20 |
| 2021/0174477 A1* | 6/2021 | Shi | G06N 20/00 |
| 2021/0196434 A1* | 7/2021 | Cramer | G06T 19/00 |
| 2021/0378793 A1* | 12/2021 | Akopov | A61C 7/08 |
| 2022/0023003 A1* | 1/2022 | Cramer | H04N 5/23222 |
| 2022/0168076 A1* | 6/2022 | Mack | B33Y 80/00 |

OTHER PUBLICATIONS

Ali et al. "Artifical NN for Prediction of Unerupted Premolars and Canines" International Medical Journal vol. 28, Supplement No. 1, pp. 74-79 Jun. 2021.*

Nanda et al. "ANN modeling and analysis for the prediction of change in the lip curvature following extraction and non-extraction orthofontic treatment" J Dent Specialities.2015;3(2):130-139.*

Muramatsu et al. "Tooth detection and classifcation on panoramic radiographs for automatic dental chart fling: improved classifcation by multi-sized input data" Oral Radiology (2021) 37:13-19.*

Tuzoff et al. "Tooth detection and numbering in panoramic radiographs using convolutional neural networks" Dentomaxillofacial Radiology (2019) 48, 20180051 © 2019 The Authors. Published by the British Institute of Radiology, pp. 1-10.*

Rani et al. "A Survey of Diagnosis of Dental Image Diseases using Soft Computing Techniques" International Journal for Research in Applied Science & Engineering Technology (IJRASET) ISSN: 2321-9653; IC Value: 45.98; SJ Impact Factor: 7.429 vol. 9 Issue V May 2021—Available at www.ijraset.com.*

* cited by examiner

FIG. 1C

FEATURE EXTRACTION ENGINE(S)
162a

MESH EXTRACTION ENGINE
172

TOOTH FEATURE DATASTORE
174

MOLAR TRIMMING PREDICTION AND VALIDATION USING MACHINE LEARNING

CROSS REFERENCE TO RELATED APPLICATIONS

This application claims the benefit of U.S. Provisional Patent Application No. 62/741,465, filed Oct. 4, 2018, titled "AUTOMATIC MOLAR TRIMMING PREDICTION AND VALIDATION USING MACHINE LEARNING," which is herein incorporated by reference in its entirety.

INCORPORATION BY REFERENCE

All publications and patent applications mentioned in this specification are incorporated herein by reference in their entirety to the same extent as if each individual publication or patent application was specifically and individually indicated to be incorporated by reference.

BACKGROUND

Orthodontic procedures may involve repositioning a patient's teeth to a desired arrangement in order to correct malocclusions and/or improve aesthetics. To achieve these objectives, orthodontic appliances such as braces, orthodontic aligners, etc. can be applied to the patient's teeth to effect desired tooth movements according to a treatment plan.

Orthodontic aligners may include devices that are removable and/or replaceable over the teeth. Orthodontic aligners may be provided as part of an orthodontic treatment plan. In some orthodontic treatment plans, a patient may be provided plurality of orthodontic aligners over the course of treatment to make incremental position adjustments to the patient's teeth.

Many orthodontic treatment plans include a processing workflow that can include performing a 3D scan of the teeth, segmenting the 3D scan into individual teeth, determining an orthodontic treatment plan, and sending the case to a doctor for review. In some situations, the 3D scan itself contains problems in the terminal molar area. For example, a molar can include portions that are not scanned (i.e., missing data), can be partially erupted, or can have gingiva covering a portion of the molar.

SUMMARY OF THE DISCLOSURE

Implementations address the need to provide an automated tooth trimming and segmentation system to effectively and accurately identify missing or incomplete data in 3D tooth models and trim or remove portions of the 3D tooth model corresponding to the missing data. Examples of missing or incomplete data include not-scanned areas, partially erupted teeth, or gingiva covering a portion of the tooth. The present application addresses these and other technical problems by providing technical solutions and/or automated agents that segment and trim 3D tooth scan data in dental patients without human intervention. Tooth trimming and segmentation may provide the basis for implementation of automated orthodontic treatment plans, design and/or manufacture of orthodontic aligners (including series of polymeric orthodontic aligners that provide forces to correct malocclusions in patients' teeth). These apparatuses and/or methods may provide or modify a treatment plan, including an orthodontic treatment plan. The apparatuses and/or methods described herein may provide instructions to generate and/or may generate a set or series of aligners, and/or orthodontic treatment plans using orthodontic aligners that incorporate the automated tooth trimming and segmentation. The apparatuses and/or methods described herein may provide a visual representation of the patient's teeth.

In general, example apparatuses (e.g., devices, systems, etc.) and/or methods described herein may acquire a representation of a patient's teeth including tooth characteristics for use as the raw features in the scoring model. The raw features may be extracted from a 3D model of the patient's teeth (e.g., a 3D tooth point cloud). In some implementations, a subset of the 3D tooth point cloud (e.g., a specific number of points representing each tooth) can be used as the raw features.

In general, example apparatuses (e.g., devices, systems, etc.) and/or methods described herein may include an automated process for determining if trimming of the molars is desired and for carrying out the trimming process. In some examples, the apparatuses and/or methods can implement machine learning classification models to determine if trimming is desired and to carry out the trimming process. Examples of machine learning systems that may be used include, but are not limited to, Convolutional Neural Networks (CNN), Decision Tree, Random Forest, Logistic Regression, Support Vector Machine, AdaBoosT, K-Nearest Neighbor (KNN), Quadratic Discriminant Analysis, Neural Network, etc. The machine learning classification models can be configured to generate an output data set that includes a probability that the data set needs to be trimmed and a location where the data set needs to be trimmed. In some examples, the machine learning classification model can output a linear scale rating (e.g., a probability between 0.0 to 1.0).

A "patient," as used herein, may be any subject (e.g., human, non-human, adult, child, etc.) and may be alternatively and equivalently referred to herein as a "patient" or a "subject." A "patient," as used herein, may but need not be a medical patient. A "patient," as used herein, may include a person who receives orthodontic treatment, including orthodontic treatment with a series of orthodontic aligners.

Any of the apparatuses and/or methods described herein may be part of a distal tooth scanning apparatus or method, or may be configured to work with a digital scanning apparatus or method.

As will be described in greater detail herein, apparatuses and/or methods described herein (e.g., for each of a patient's teeth) may include collecting a 3D scan of the patient's teeth. Collecting the 3D scan may include taking the 3D scan, including scanning the patient's dental arch directly (e.g., using an intraoral scanner) or indirectly (e.g., scanning an impression of the patient's teeth), acquiring the 3D scan information from a separate device and/or third party, acquiring the 3D scan from a memory, or the like. The 3D scan can generate a 3D mesh of points representing the patient's arch, including the patient's teeth and gums.

Additional information may be collected with the 3D scan, including patient information (e.g., age, gender, etc.).

The 3D scan information may be standardized and/or normalized. Standardizing the scan may include converting the 3D scan into a standard format (e.g., a tooth surface mesh), and/or expressing the 3D scan as a number of angles (e.g., vector angles) from a center point of each tooth, etc. In some variations, standardizing may include normalizing the 3D scan using another tooth, including stored tooth values.

Standardizing may include identifying a predetermined number of angles relative to a center point of the target tooth.

Any appropriate method may be used to determine the center of the tooth. For example, the center of the tooth may be determined from a mesh point representation of each tooth (e.g., from a segmented version of the 3D scan representing a digital model of the patient's teeth) by determining the geometric center of the mesh points for each tooth, by determining the center of gravity of the segmented tooth, etc. The same method for determining the center of each tooth may be consistently applied between the teeth and any teeth used to form (e.g., train) the systems described herein.

Standardizing may be distinct from normalizing. As used herein, standardizing may involve regularizing numerical and/or other description(s) of a tooth. For example, standardizing may involve regularizing the order and/or number of angles (from the center of the tooth) used to describe the teeth. The sizes of the teeth from the original 3D scan may be maintained.

Any appropriate features may be extracted from the prepared (e.g., standardized and/or normalized) teeth. For example, in some variations, features may include a principal component analysis (PCA) for each of the teeth in the dental arch being examined. Additional features (e.g., geometric descriptions of the patient's teeth) may not be desired (e.g., PCA alone may be used) or it may be used to supplement the PCA of each tooth. PCA may be performed on the standardized teeth using any appropriate technique, as discussed above, including using modules from existing software environments such C++ and C# (e.g., ALGLIB library that implements PCA and truncated PCA, MLPACK), Java (e.g., KNIME, Weka, etc.), Mathematica, MATLAB (e.g., MATLAB Statistics Toolbox, etc.), python (e.g., numpy, Scikit-learn, etc.), GNU Octave, etc.

In some examples, the apparatuses and/or methods herein may segment a patient's teeth from the 3D scan information without human intervention, and this segmentation information may be used to simulate, modify and/or choose between various orthodontic treatment plans. For example, segmentation can be performed by a computing system by evaluating data (such as three-dimensional scan, or a dental impression) of the patient's teeth or arch to separate the 3D mesh of points into individual teeth and gums.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1C is a diagram showing an example of a feature extraction engine(s).

DETAILED DESCRIPTION

Figure 1A:
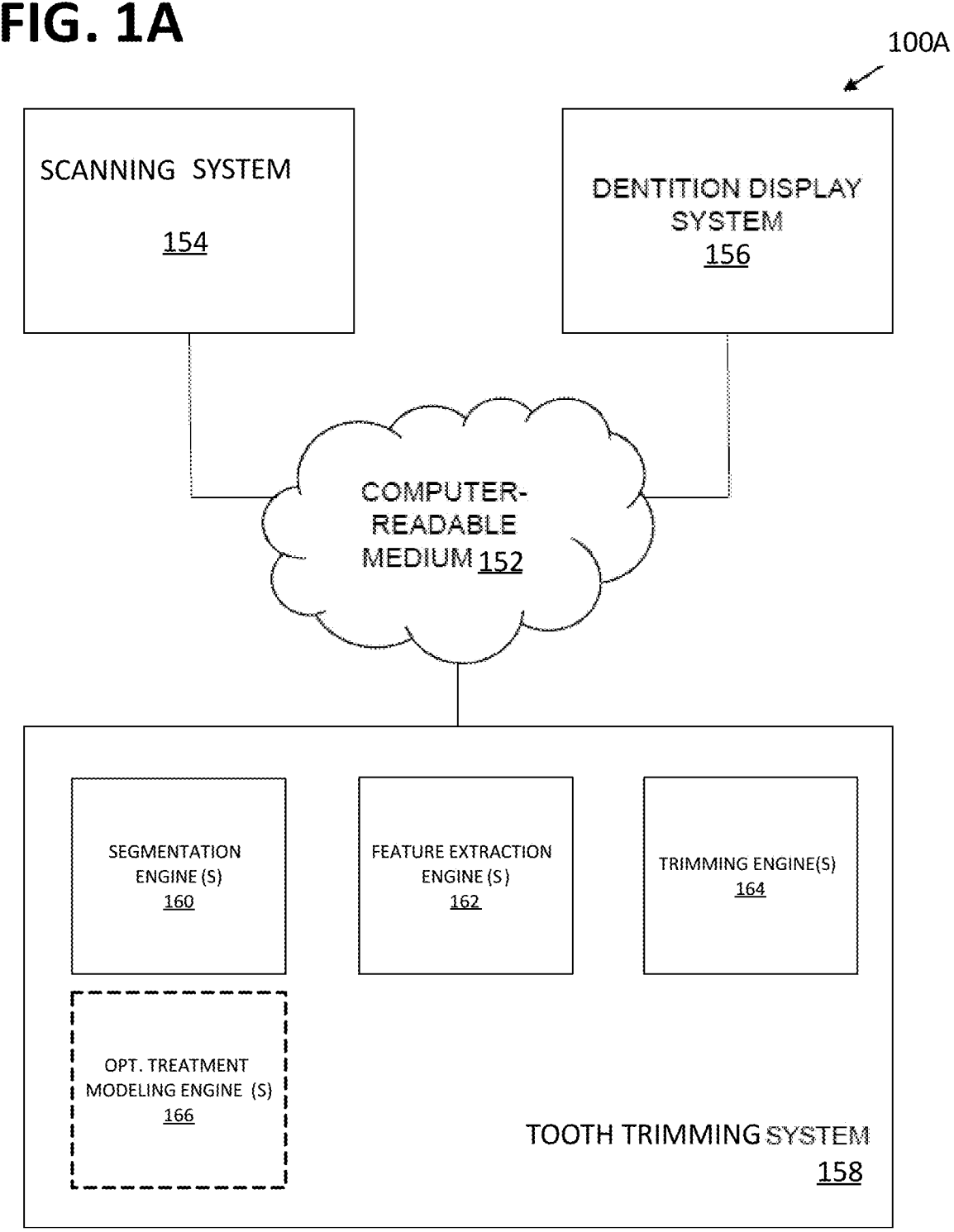
FIG. 1A is a diagram showing an example of a computing environment configured to digitally scan a dental arch, identify missing data in 3D tooth scans, and trim or remove portions of the 3D tooth model corresponding to the missing data.

Described herein are apparatuses (e.g., systems, computing device readable media, devices, etc.) and methods for accurately identifying missing or incomplete data in 3D tooth models and removing portions of the 3D tooth model corresponding to the missing or incomplete data. One object of the present disclosure is to use machine learning technology to provide a classifier that can determine if a 3D tooth model representing one or more of the patient's teeth needs to be trimmed and to trim and/or remove the data from the 3D tooth model corresponding to the tooth that needs to be trimmed. A "classifier," as used herein, may incorporate one or more automated agents to predict one or more classes of given data points. A classifier can include machine learning techniques, as discussed further herein. The word "trimming," (and variants "trim," "trimmed," etc.) as used herein, may include computer-implemented operations to remove at least a part of a 3D tooth model. Examples of trimming operations include removing part of representations of molars, bicuspids, canines, incisors, etc., from a 3D tooth model. Trimming can be used in conjunction with modeling treatment plans. For some treatment plans, it may be desirable to remove parts of a molar (e.g., molars with portions that are not scanned (i.e., missing data), molars that are partially erupted, and/or molars having gingiva covering a portion thereof) from a 3D tooth model. The classifier can make such determinations based upon various data including patient demographics, tooth measurements, tooth surface mesh, processed tooth features, and historical patient data. These methods and apparatus can use this information to provide an output that indicates a probability that trimming is desirable and/or location(s) to be trimmed. Such determinations may form the basis of treatment planning by creating 3D tooth models that are useful for treatment planning and/or fabrication of orthodontic appliances implementing such treatment plans.

For example, described herein are apparatuses and/or methods, e.g., systems, including systems to implement processes that incorporate a tooth trimming system without human intervention. When the system is triggered by a request for a trimming assessment, the system can retrieve relevant tooth/patient information from a local or remote database, process the information, and convert the information into representative features. The features can be passed into a trimming classification model, which may use machine learning technology (e.g., Convolutional Neural Network (CNN), Decision Tree, Random Forest, Logistic Regression, Support Vector Machine, AdaBOOST, K-Nearest Neighbor (KNN), Quadratic Discriminant Analysis, Neural Network, etc.) to return a probability that 3D tooth model representing the patient's teeth needs to be trimmed, and the location to be trimmed. The parameters inputted into the tooth scoring classification model can be optimized with historic data. The tooth trimming classification model may be used to provide an output indicating the probability that 3D tooth model of the patient's teeth requires trimming and the location of the tooth or teeth that need to be trimmed. The results may be provided on demand and/or may be stored in a memory (e.g., database) for later use.

The apparatuses and/or methods described herein may be useful in planning and fabrication of dental appliances, including elastic polymeric positioning appliances, is described in detail in U.S. Pat. Nos. 5,975,893, 6,409,504, and in published PCT application WO 98/58596, which is herein incorporated by reference for all purposes. Systems of dental appliances employing technology described in U.S. Pat. No. 5,975,893 are commercially available from Align Technology, Inc., Santa Clara, Calif., under the tradename, Invisalign System.

Throughout the body of the Description of Embodiments, the use of the terms "orthodontic aligner", "aligner", or "dental aligner" is synonymous with the use of the terms "appliance" and "dental appliance" in terms of dental applications. For purposes of clarity, embodiments are hereinafter described within the context of the use and application of appliances, and more specifically "dental appliances."

FIG. 1A is a diagram showing an example of a computing environment 100A configured to facilitate gathering digital scans of a dental arch with teeth therein. The environment 100A includes a computer-readable medium 152, a scanning system 154, a dentition display system 156, and a tooth trimming system 158. One or more of the modules in the computing environment 100A may be coupled to one another or to modules not explicitly shown.

The computer-readable medium 152 and other computer readable media discussed herein are intended to represent a variety of potentially applicable technologies. For example, the computer-readable medium 152 can be used to form a network or part of a network. Where two components are co-located on a device, the computer-readable medium 152 can include a bus or other data conduit or plane. Where a first component is co-located on one device and a second component is located on a different device, the computer-readable medium 152 can include a wireless or wired back-end network or LAN. The computer-readable medium 152 can also encompass a relevant portion of a WAN or other network, if applicable.

The scanning system 154 may include a computer system configured to scan a patient's dental arch. A "dental arch," as used herein, may include at least a portion of a patient's dentition formed by the patient's maxillary and/or mandibular teeth, when viewed from an occlusal perspective. A dental arch may include one or more maxillary or mandibular teeth of a patient, such as all teeth on the maxilla or mandible or a patient. The scanning system 154 may include memory, one or more processors, and/or sensors to detect contours on a patient's dental arch. The scanning system 154 may be implemented as a camera, an intraoral scanner, an x-ray device, an infrared device, etc. The scanning system 154 may include a system configured to provide a virtual representation of a physical mold of patient's dental arch. The scanning system 154 may be used as part of an orthodontic treatment plan. In some implementations, the scanning system 154 is configured to capture a patient's dental arch at a beginning stage, an intermediate stage, etc. of an orthodontic treatment plan.

The dentition display system 156 may include a computer system configured to display at least a portion of a dentition of a patient. The dentition display system 154 may include memory, one or more processors, and a display device to display the patient's dentition. The dentition display system 156 may be implemented as part of a computer system, a display of a dedicated intraoral scanner, etc. In some implementations, the dentition display system 156 facilitates display of a patient's dentition using scans that are taken at an earlier date and/or at a remote location. It is noted the dentition display system 156 may facilitate display of scans taken contemporaneously and/or locally to it as well. As noted herein, the dentition display system 156 may be configured to display the intended or actual results of an orthodontic treatment plan applied to a dental arch scanned by the scanning system 154. The results may include 3D virtual representations of the dental arch, 2D images or renditions of the dental arch, etc.

The tooth trimming system 158 may include a computer system configured to process 3D scans or meshes of a patient's dentition taken by the scanning system 154. As noted herein, the tooth trimming system 158 may be configured to determine a probability that the 3D tooth model of the patient's dentition requires trimming, and may also be configured to trim the 3D tooth model. The tooth trimming system 158 may include segmentation engine(s) 160, feature extraction engine(s) 162, and trimming engine(s) 164. One or more of the modules of the image trimming system 158 may be coupled to each other or to modules not shown.

As used herein, any "engine" may include one or more processors or a portion thereof. A portion of one or more processors can include some portion of hardware less than all of the hardware comprising any given one or more processors, such as a subset of registers, the portion of the processor dedicated to one or more threads of a multi-threaded processor, a time slice during which the processor is wholly or partially dedicated to carrying out part of the engine's functionality, or the like. As such, a first engine and a second engine can have one or more dedicated processors or a first engine and a second engine can share one or more processors with one another or other engines. Depending upon implementation-specific or other considerations, an engine can be centralized or its functionality distributed. An engine can include hardware, firmware, or software embodied in a computer-readable medium for execution by the processor. The processor transforms data into new data using implemented data structures and methods, such as is described with reference to the figures herein.

The engines described herein, or the engines through which the systems and devices described herein can be implemented, can be cloud-based engines. As used herein, a cloud-based engine is an engine that can run applications and/or functionalities using a cloud-based computing system. All or portions of the applications and/or functionalities can be distributed across multiple computing devices, and need not be restricted to only one computing device. In some embodiments, the cloud-based engines can execute functionalities and/or modules that end users access through a web browser or container application without having the functionalities and/or modules installed locally on the end-users' computing devices.

As used herein, "datastores" may include repositories having any applicable organization of data, including tables, comma-separated values (CSV) files, traditional databases (e.g., SQL), or other applicable known or convenient organizational formats. Datastores can be implemented, for example, as software embodied in a physical computer-readable medium on a specific-purpose machine, in firmware, in hardware, in a combination thereof, or in an applicable known or convenient device or system. Datastore-associated components, such as database interfaces, can be considered "part of" a datastore, part of some other system component, or a combination thereof, though the physical location and other characteristics of datastore-associated components is not critical for an understanding of the techniques described herein.

Datastores can include data structures. As used herein, a data structure is associated with a particular way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. The datastores, described herein, can be cloud-based datastores. A cloud-based datastore is a datastore that is compatible with cloud-based computing systems and engines.

The segmentation engine(s) 160 may be configured to implement one or more automated agents configured to process tooth scans from the scanning system 154. The segmentation engine(s) 160 may include graphics engines to process images or scans of a dental arch. In some implementations, the segmentation engine(s) 160 format scan data from an scan of a dental arch into a dental mesh model (e.g., a 3D tooth model) of the dental arch. In other embodiments, the segmentation engine(s) 160 can format 2D or 3D images of the dental arch into a dental mesh model. For example, multiple 2D images of the patient's teeth can be input into the segmentation engine(s) 160 to form the dental mesh model. The 2D images can comprise, for example, multiple images of the patient's teeth. In some embodiments, the patient's dental arch is divided into quarters, and multiple input 2D images for each quarter of the patient's dental arch can be used to generate the dental mesh model. The segmentation engine(s) 160 may also be configured to segment the 3D dental mesh model of the dental arch into individual dental components, including segmenting the 3D tooth model into 3D tooth models of individual teeth. The 3D tooth models of the dental arch and/or the individual teeth may comprise geometric point clouds or polyhedral objects that depict teeth and/or other elements of the dental arch in a format that can be rendered on the dentition display system 156. In some implementations, the segmentation engine(s) 160 may determine the center of one or more individual teeth of the 3D tooth model. The center of the tooth may be determined from a mesh point representation of each tooth (e.g., from a segmented version of the 3D scan representing a digital model of the patient's teeth) by determining the geometric center of the mesh points for each tooth, by determining the center of gravity of the segmented tooth, etc. The segmentation engine(s) 160 may provide 3D tooth models and/or other data, such as individual teeth centers, to other modules of the tooth trimming system 158.

The feature extraction engine(s) 162 may implement one or more automated agents configured to extract dental features. A "dental feature," as used herein, may include data points from the 3D dental mesh model that correlate to geometrical properties (e.g., edges, contours, vertices, vectors, surfaces, etc.) of the patient's teeth. A "dental feature" may be based on patient demographics and/or tooth measurements. A dental feature may be related to "PCA features," e.g., those dental features derived from a principal component analysis (PCA) of a tooth. In some implementations, the feature extraction engine(s) 162 is configured to analyze 3D dental mesh models from the segmentation engine(s) 160 to extract the dental features. In one implementation, the feature extraction engine(s) 162 may, for each tooth under consideration, extract a subset of dental features from the 3D tooth model. For example, a specified number of tooth measurement points (e.g., nine tooth measurement points) can be extracted. This subset of measurement points can be selected to define the position and orientation of each tooth, as well as partial information on the tooth shape.

The trimming engine(s) 164 may implement one or more automated agents configured to predict a probability that the 3D tooth model of a patient's teeth (or portion thereof) relate to one or more trimming factors. "Trimming factors," as used herein, may include any factors that form the basis of a trimming determination, e.g., a determination whether or not to trim a part of a 3D tooth model and/or the parts of a 3D model where trimming is desirable. In some implementations, the trimming engine(s) 164 may determine whether trimming is desired and/or may also identify location(s), specific tooth, and/or specific teeth within the 3D tooth model for which trimming would be desirable. In some implementations, the trimming engine(s) 164 assign physical and/or geometrical properties to a 3D dental mesh model that are related to physical/geometrical properties of dental arches or teeth. The trimming engine(s) 164 may acquire dental features from the feature extraction engine(s) 162 and apply machine learning algorithms to predict if it would be desirable to trim the 3D tooth model representing the patient's teeth; it may also predict the location, tooth, or teeth for which trimming would be desirable. In some implementations, the trimming engine(s) 164 use a trained convolutional neural network and/or trained classifiers to identify a probability that trimming would be desirable for one or more teeth on a 3D tooth model. Examples of machine learning systems implemented by the trimming engine(s) 164 may include Decision Tree, Random Forest, Logistic Regression, Support Vector Machine, AdaBOOST, K-Nearest Neighbor (KNN), Quadratic Discriminant Analysis, Neural Network, etc., to perform the trimming assessment.

If trimming is desired, the trimming engine(s) 164 may further implement one or more automated agents configured to identify an orientation and position of a trim plane. A "trim plane," as used herein, may include a plane that passes through a 3D virtual model and forms the basis of a trimming determination. Proper placement of the trim plane ensures that any problem areas in the scan or 3D dental mesh model are removed, but enough of the scan or 3D dental mesh model remains to allow for construction or manufacturing of a dental aligner. In some implementations, the trimming engine(s) may use the segmented model of the patient's teeth to build a parametric model representing an arch portion corresponding to the patient's teeth. The parametric model can comprise, for example, a quadratic Bezier curve. In some implementations, the trimming engine(s) can find a trim plane normal vector on at least one of the teeth as a tangent to the parametric model. For example, the trimming engine(s) can find a trim plane normal vector at a corresponding last (or distal-most) molar center of the parametric model. In some implementations, the trim plane normal vector can be further adjusted by tooth axes. The trimming engine can trim the appropriate location, tooth, or teeth, and the trimmed location, tooth, or teeth can be incorporated into a final segmentation result.

The optional treatment modeling engine(s) 166 may be configured to store and/or provide instructions to implement orthodontic treatment plans and/or the results of orthodontic treatment plans. The optional treatment modeling engine(s) 166 may provide the results of orthodontic treatment plans on a 3D dental mesh model. The optional treatment modeling engine(s) 166 may model the results of application of orthodontic aligners to the patient's dental arch over the course of an orthodontic treatment plan.

Figure 1B:
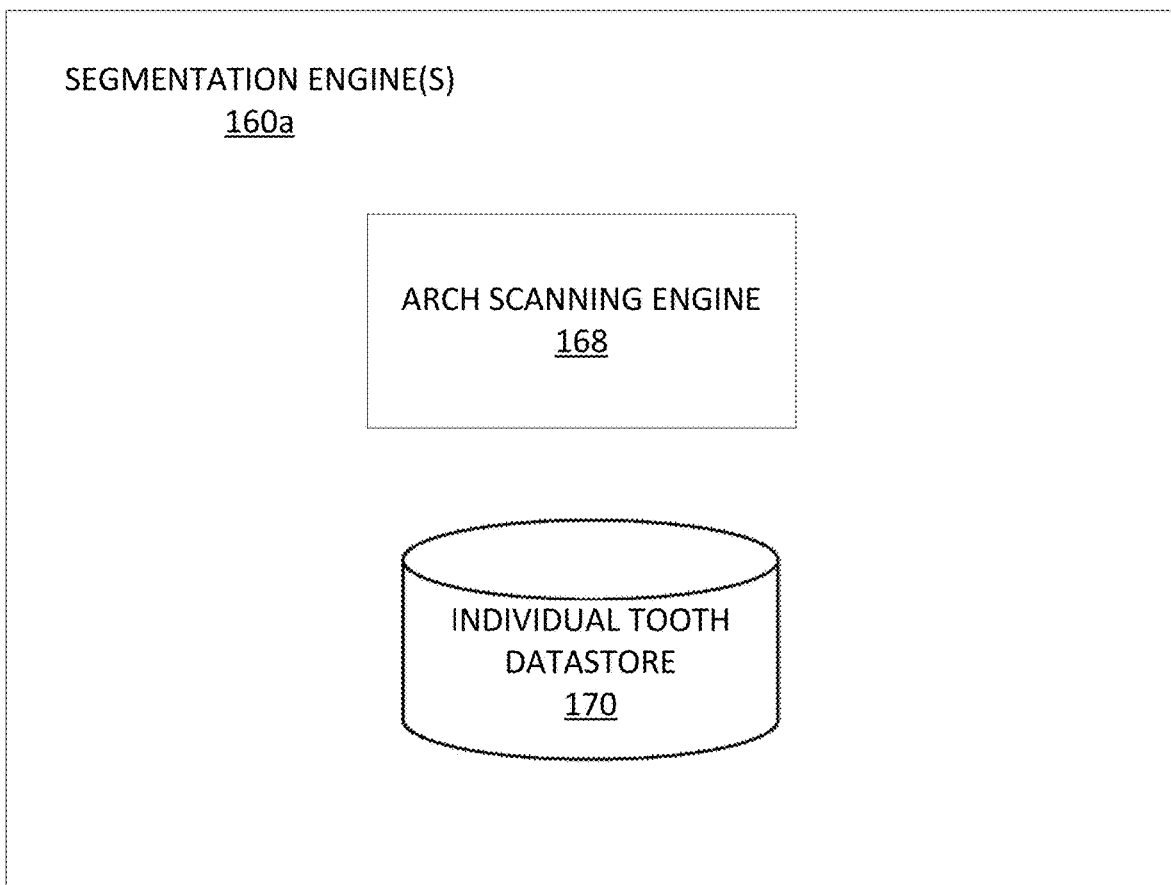
FIG. 1B is a diagram showing an example of segmentation engine(s).

FIG. 1B is a diagram showing an example of the segmentation engine(s) 160*a*. The segmentation engine(s) 160*a* may include an arch scanning engine 168 and an individual tooth segmentation datastore 170. One or more of the modules of the segmentation engine(s) 160*a* may be coupled to each other or to modules not shown.

The arch scanning engine 168 may implement one or more automated agents configured to scan a scan of the patient's teeth, 2D or 3D images of the patient's teeth, or a 3D dental mesh model for individual tooth segmentation data. "Individual tooth segmentation data," as used herein, may include positions, geometrical properties (contours, etc.), tooth centers, and/or other data that can form the basis of segmenting individual teeth from 3D dental mesh models of a patient's dental arch. The arch scanning engine 168 may implement automated agents to separate dental mesh data for individual teeth from a 3D dental mesh model of the dental arch. The arch scanning engine 168 may implement automated agents to determine the center of individual teeth from a mesh point representation of each tooth by determining the geometric center of the mesh points for each tooth, by determining the center of gravity of the segmented tooth, etc. The arch scanning engine 168 may further implement automated agents to number the individual teeth.

In embodiments where the inputs to the arch scanning engine 168 comprise 2D or 3D images of the patient's teeth, the images can comprise, for example, multiple images of the patient's teeth. In some embodiments, the patient's dental arch is divided into quarters, and multiple input 2D images for each quarter of the patient's dental arch can be used to generate the dental mesh model and/or to scan for individual tooth segmentation data. In one embodiment, the resolution of the images can be 256×256 for each view (there can be multiple views per each quarter, such as four views per quarter). Each quarter of the dental arch can include its own machine learning network to scan for segmentation data. For each view, a machine learning network with a plurality of layers can be used as an encoder with some additional "fully connected" layers to fuse activation from each views. In a specific embodiment, with a resolution of 256×256, the size of weights is 429 Mb for each network. Potentially these weights can be compressed by sharing parameters between branches. Thus, in one embodiment the system requires at least 750 Mb in RAM to predict trimming for a given quarter.

The individual tooth segmentation datastore 170 may be configured to store data related to model dental arches, including model dental arches that have been segmented into individual teeth. The model dental arch data may comprise data related to segmented individual teeth, including individual tooth centers, and tooth identifiers of the individual teeth such as tooth types and tooth numbers.

FIG. 1C is a diagram showing an example of a feature extraction engine(s) 162*a*. The feature extraction engine(s) 162*a* may include a mesh extraction engine 172 and a tooth feature datastore 174. One or more of the modules of the feature extraction engine(s) 162*a* may be coupled to each other or to modules not shown.

The mesh extraction engine 172 may implement one or more automated agents configured to determine or extract raw features from the individual tooth segmentation data. The tooth shape features may comprise, for example, the 3D point cloud, or alternatively, a subset of data points from the 3D point cloud specifically chosen to represent the shape, position, and orientation of the tooth.

The mesh extraction engine 172 may also implement one or more automated agents configured to produce features for the scoring model. In one example, principal component analysis (PCA) can be implemented to obtain the dental features that will be used by the scoring model. In one implementation, the 3D dental mesh model of individual teeth comprises a scatter plot of points representing a patient's tooth, and PCA can be applied to the scatter plot to obtain vectors along the biggest distribution of scatter plots. In another example, the mesh extraction engine 172 may implement automated feature exploration (e.g., using deep neural networks or other feature selection methods) to produce the features for the scoring model.

The tooth feature datastore 176 may be configured to store data related to raw features or produced features from the modules described above.

Figure 1D:
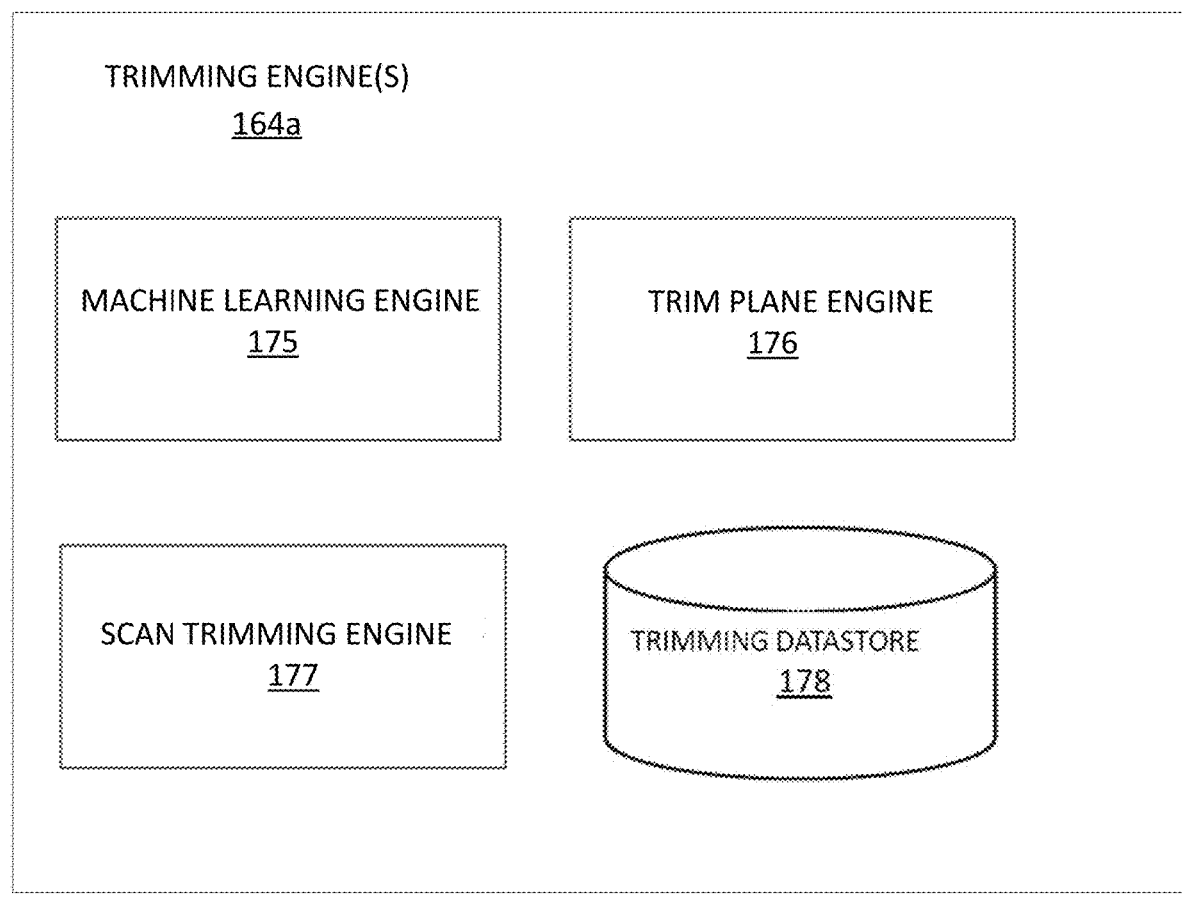
FIG. 1D is a diagram showing an example of a trimming engine(s).
Figure 2A:
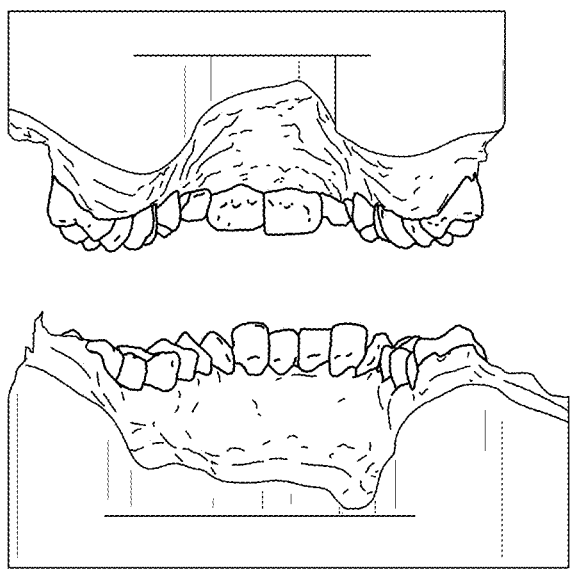
FIGS. 2A-2F illustrate one example of an input for a trimming engine comprising a 3D model of the patient's teeth (showing six views).
Figure 2B:
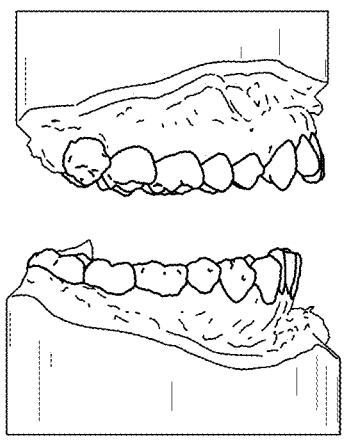
Figure 2C:
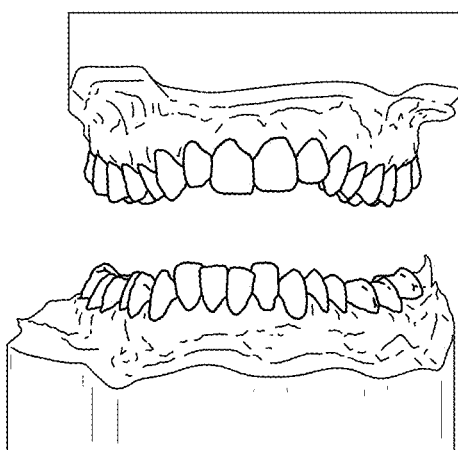
Figure 2D:
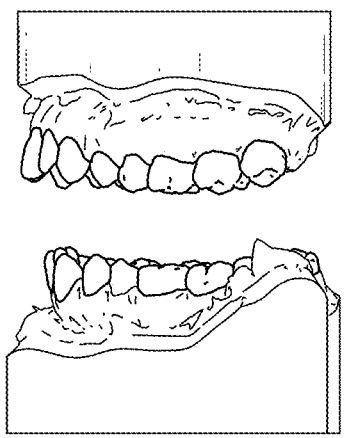
Figure 2E:
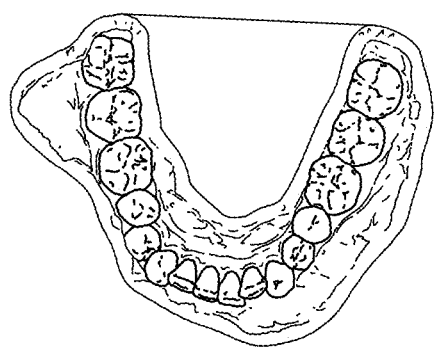
Figure 2F:
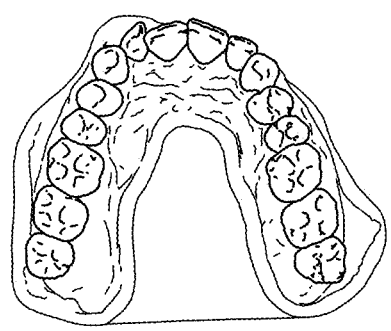

FIG. 1D is a diagram showing an example of the trimming engine(s) 164*a*. The trimming engine(s) 164*a* may acquire raw and/or produced feature data from the feature extraction engine(s) 162*a* described above. The trimming engine(s) 164*a* may include a machine learning engine 175, a trim plane engine 176, a scan trimming engine 177, and a trimming datastore 178. FIGS. 2A-2F illustrate one example of an input for the trimming engine(s) 164*a*, comprising a 3D model of the patient's teeth (shown from various views) from the arch scanning engine including features from the mesh extraction engine. For example, the 3D tooth model in FIGS. 2A-2F may include individually segmented teeth that provide representations of the shape of each of the patient's teeth. In some examples, the input can include depth maps of the teeth.

The machine learning engine 175 may implement one or more automated agents configured to use machine learning techniques to classify a probability that 3D tooth model of a patient's teeth requires trimming and to identify the location to be trimmed. In some implementations, the machine learning engine 175 may acquire raw features and/or produced features data from the feature extraction engine(s) 162*a*. Using a trained classifier, the machine learning engine 175 may provide an identifier (e.g., a statistical or other score) that determines a probability that the 3D scan needs to be trimmed. The machine learning engine 175 may further provide a location within the 3D tooth model that requires trimming (e.g., identifying the individual tooth that requires trimming).

As examples, the machine learning engine 175 may use a classifier trained to correlate various dental features with whether the 3D tooth model requires trimming. More specifically, the classifier may be trained to compare the geometry of a target tooth (e.g., an individually segmented molar from the 3D tooth model) to the ideal or general shape associated with that target tooth. The classifier can then return a score that assesses how accurately the target tooth tracks the ideal or general tooth shape. The classifier can further identify the location within the 3D tooth model, or the individual tooth segmentation, that requires trimming.

The machine learning engine 175 may incorporate one or more machine learning techniques. Examples of such techniques include Convolutional Neural Networks (CNN), Decision Tree, Random Forest, Logistic Regression, Support Vector Machine, AdaBOOST, K-Nearest Neighbor (KNN), Quadratic Discriminant Analysis, Neural Network, etc. The machine learning engine 175 can provide an output with a probability that the 3D tooth model of the patient's teeth requires trimming and the location of the tooth or teeth that requires trimming. The output can be, for example, a linear score or a percentage (e.g., 0.0 to 1.0, 0 to 10, 0% to 100%), a categorical output (e.g., "No Trim", "Most Likely No Trim", "Likely Not Trim", "Likely Trim", "Most Likely Trim", "Trim", etc.), and optionally, a graphical representation of a 3D model of the teeth identifying the location that needs trimming.

Figure 3:
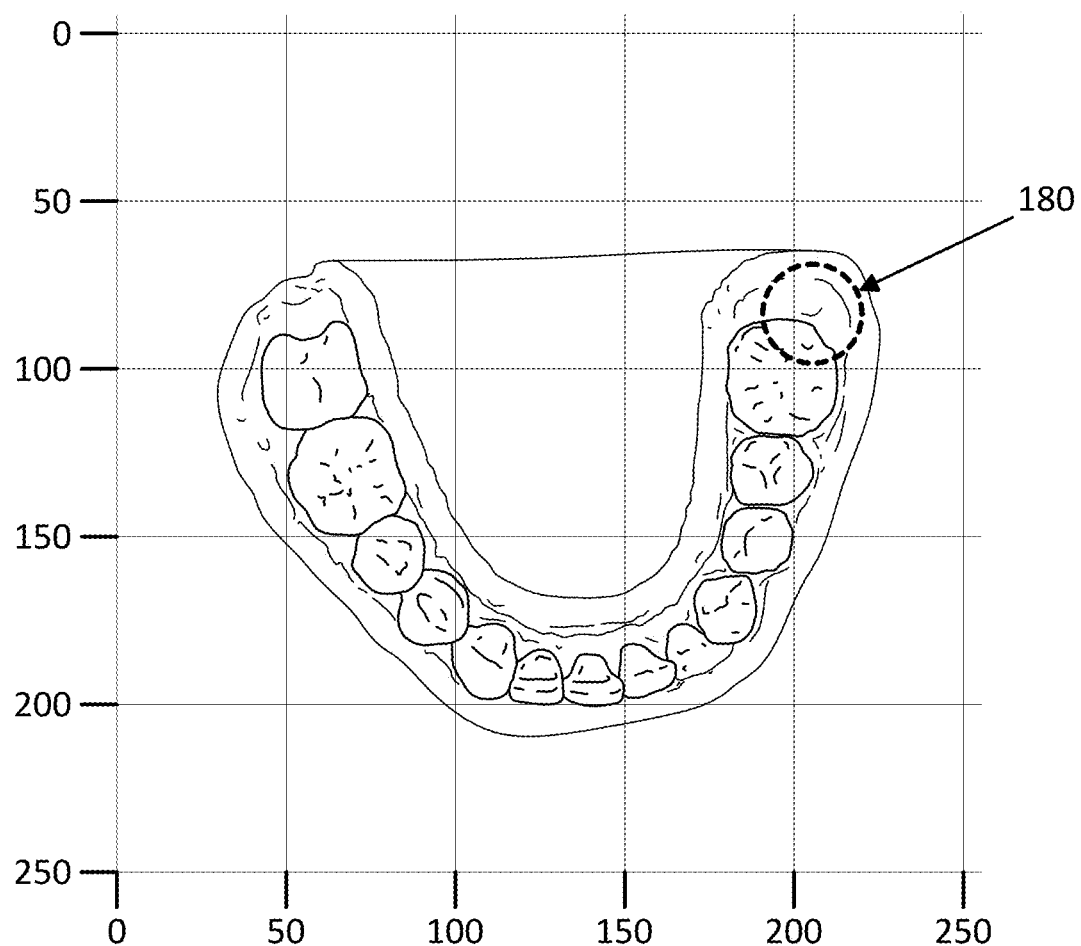
FIG. 3 shows one example of an output of a machine learning engine as described herein.

When the machine learning engine has determined that the 3D tooth model of the patient's teeth requires trimming with a sufficiently high probability, the system can optionally output a graphical representation of the location of the 3D tooth model that requires trimming. FIG. 3 is an example of an optional graphical output of the machine learning engine 175, which identifies on the 3D tooth model the location, tooth, or teeth in the 3D tooth model that requires trimming. In this example, the machine learning engine 175 indicates the need for trimming in the location identified by region 180. Additionally, the graphical output can further include a numerical or written probability that the identified location requires trimming (e.g., a percentage or linear output as described above).

The trim plane engine 176 may implement one or more automated agents configured to identify a position and/or orientation of a trim plane or trim planes within the 3D tooth model. In some implementations, the trimming engine(s) may use the segmented model of the patient's teeth to build a parametric model representing an arch portion corresponding to the patient's teeth. The parametric model can comprise, for example, a quadratic Bezier curve, however it should be understood that other specific parametric models can be used.

Figure 4A:
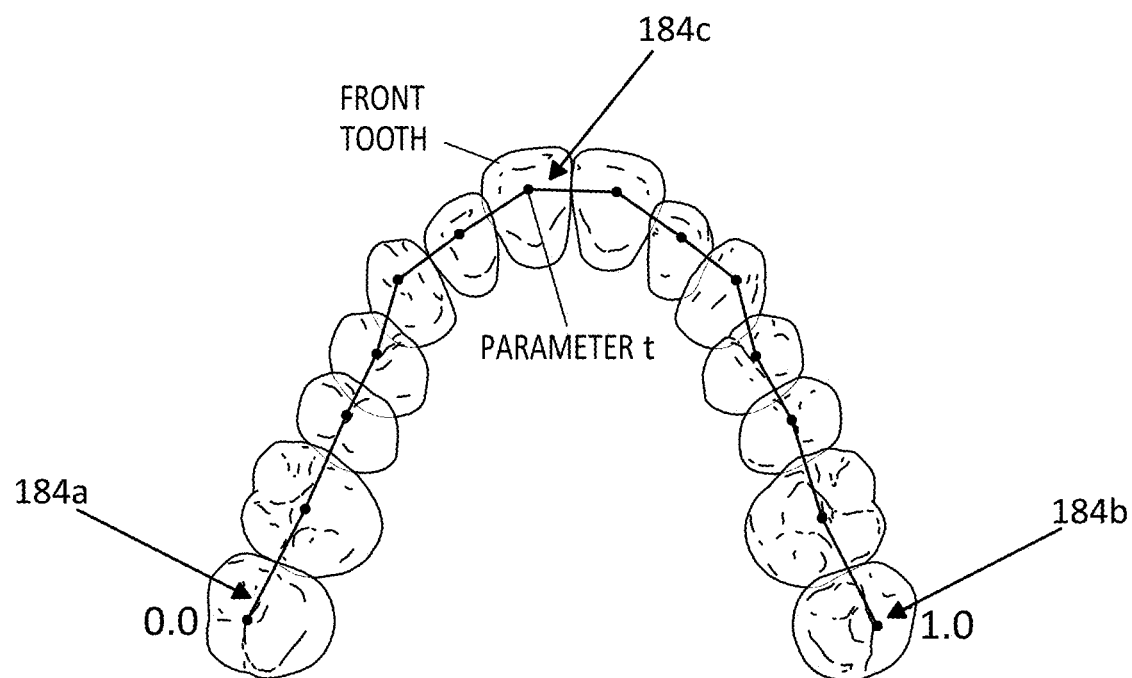
FIGS. 4A-4B illustrate building a parametric model to identify a trim plane.
Figure 4B:
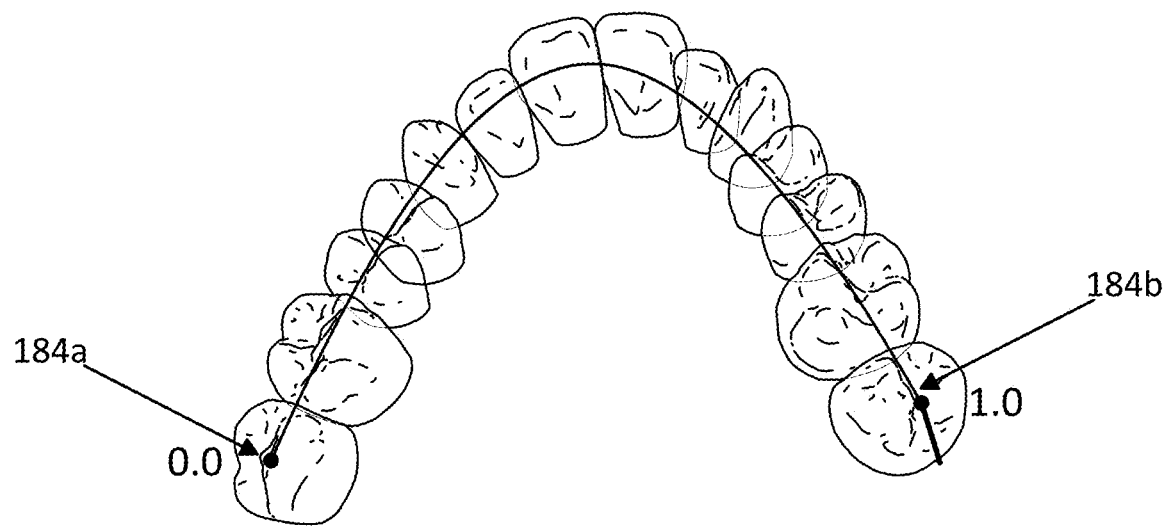

Referring to FIGS. 4A-4B, the trim plane engine can use a plurality of tooth features to build the parametric model. Generally, at least three tooth features are needed to build the parametric model, including preferably a tooth feature from a distal tooth on the left side of a jaw, a tooth feature from a mesial and/or centrally located tooth (e.g., incisors or canines), and a tooth feature from a distal tooth on the right side of the jaw. In FIG. 4A, for example, at least tooth center points 184*a* and 184*b* of the two distal-most molars (e.g., on the left and right side, respectively) and an incisor center point 184*c* can be used to build the parametric model. While tooth centers are the tooth features used to build the parametric model in the illustrated example, it should be understood that other tooth features can be used to build the model, including but not limited to lingual, buccal, or occlusal surfaces, gaps or spaces between teeth, or specific structures on or around the patient's teeth. Still referring to FIG. 4A, straight lines connecting adjacent tooth features provides an initial representation of the parametric model. FIG. 4B is an illustration in which the parametric model has been applied to the input tooth features to provide a smooth curve representative of the patient's dental arch associated with those input tooth features.

The trim plane engine 176 may further implement one or more automated agents to find a trim plane normal vector as a tangent to the parametric model. In some implementations, the trim plane normal vector is the tangent line to the curve of the parametric model at the tooth feature of the distal-most, or last input tooth. For example, referring to FIG. 4B, the trim plane engine can be configured to find the tangent line to the parametric model at the tooth center point 184*b* of the distal-most molar on the right side of the jaw. In the example where the parametric model comprises a Bezier curve, the trim plane engine can be configured to find the tangent line to the Bezier curve at either parameter 0.0 or 1.0 on the Bezier curve.

Figure 4C:
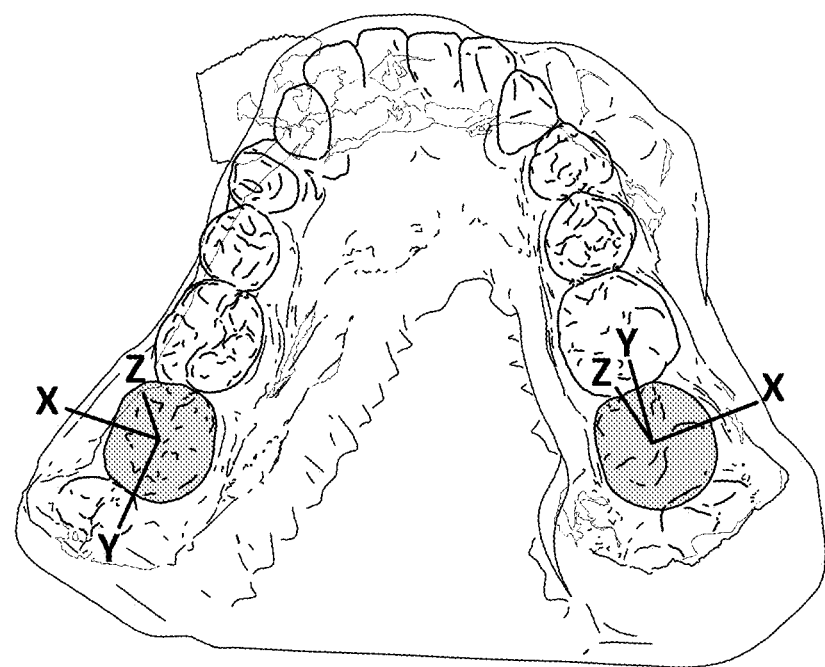
FIGS. 4C-4E illustrate adjusting the trim plane by tooth axes.

Once the trim plane engine has found the trim plane normal vector, as described above, the trim plane engine can further implement one or more automated agents to adjust and fine tune the orientation of the trim plane normal vector with adjustments along tooth axes, including along the x-axis (e.g., moving to the buccal side of the tooth), along the y-axis (e.g., moving in the mesial direction for teeth on the right side of the jaw or moving in the distal direction for teeth on the left side of the jaw), and along the z-axis (e.g., going up from the lower jaw or down from the upper jaw). FIG. 4C is an illustration showing the tooth axes for both the distal-most molars in a patient's jaw.

Figure 4D:
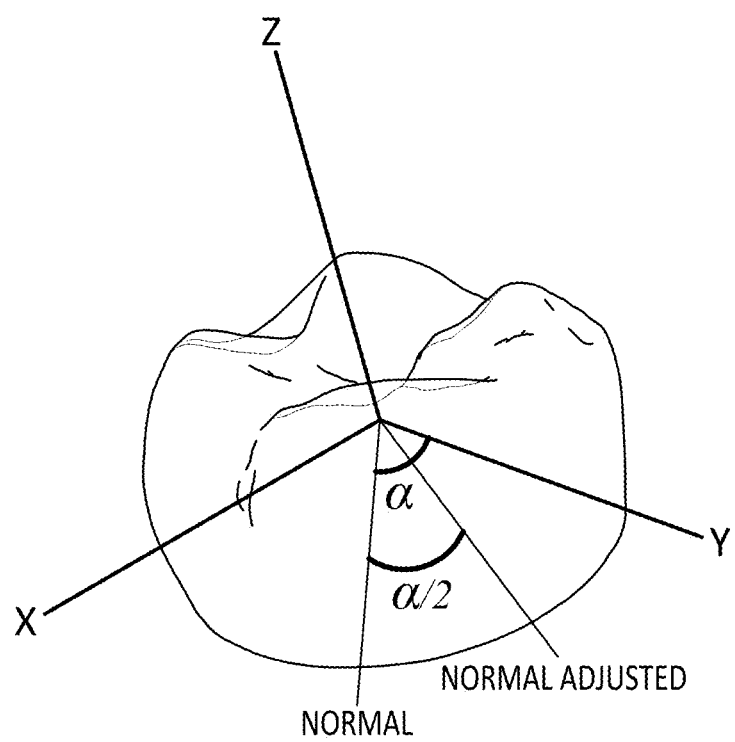

Referring to FIG. 4D, the trim plane normal vector can be adjusted by rotating the normal vector around the tooth z-axis in the direction of the tooth y-axis. In some embodiments, the rotation angle is the minimum of either half the angle α between the normal vector and the tooth y-axis or a pre-determined rotation angle. In one example, the predetermined rotation angle can be 7.5 degrees. FIG. 4D is an illustration showing an adjusted orientation of the trim plane normal vector in the direction of the tooth y-axis.

Figure 4E:
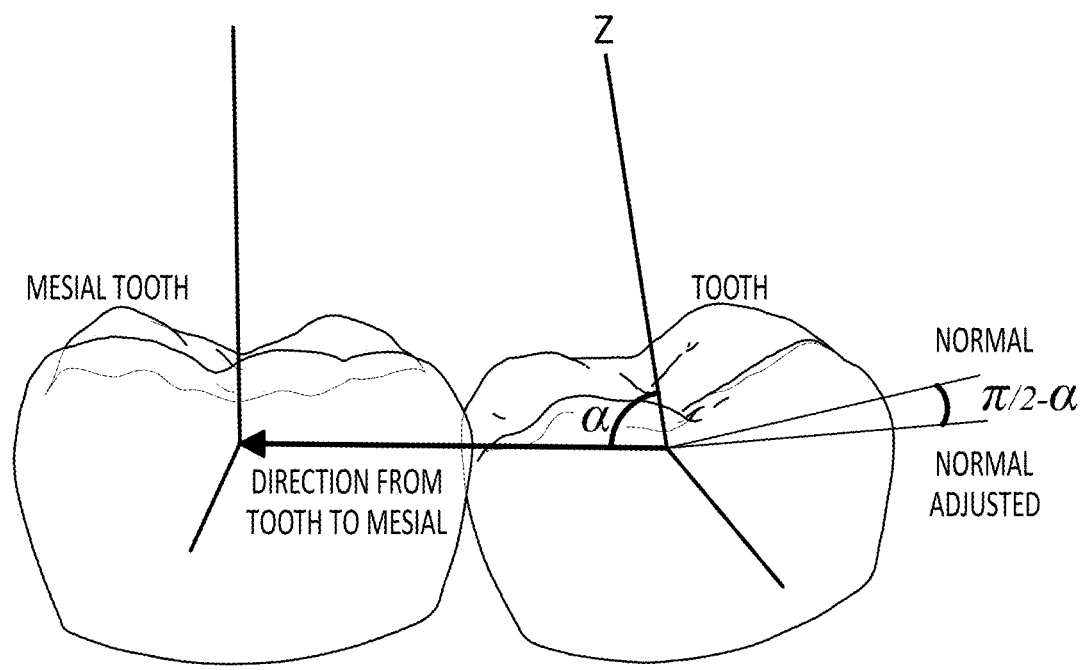
Figure 5A:
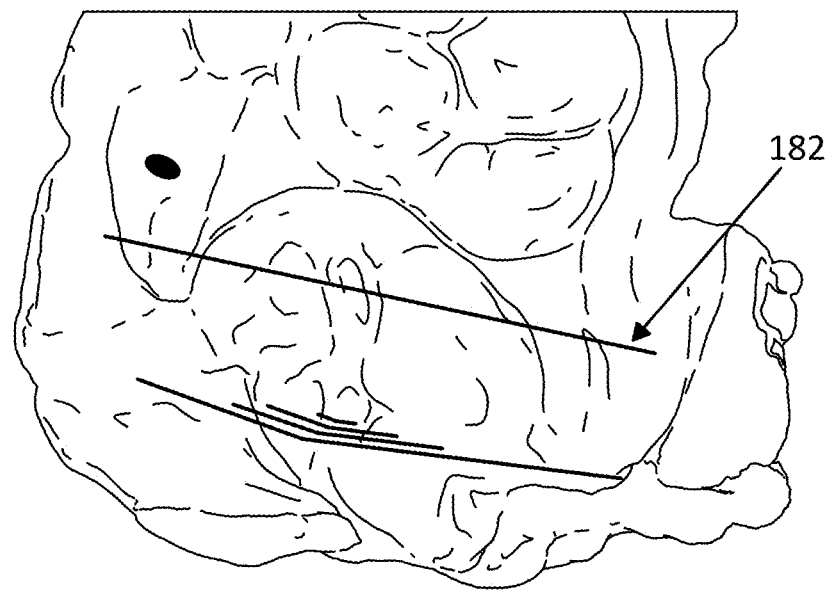
FIGS. 5A-5E illustrate examples of a tooth (e.g., a molar) that requires trimming as identified by a machine learning engine described herein.
Figure 5B:
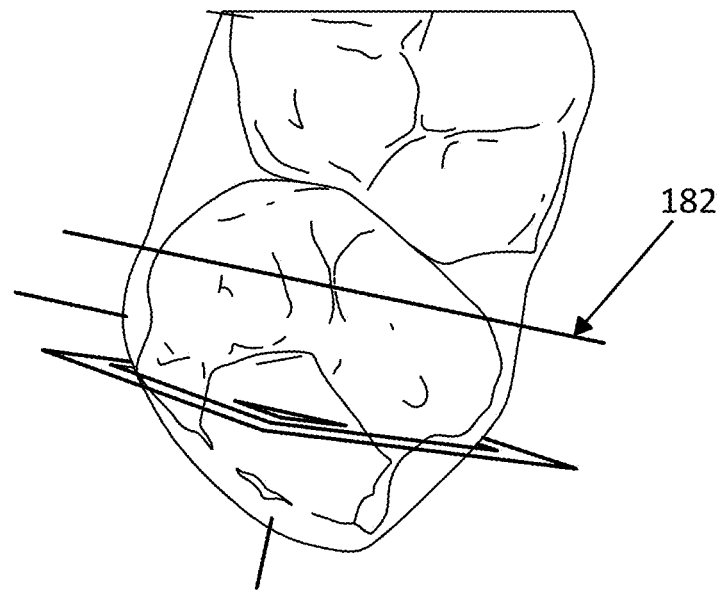
Figure 5C:
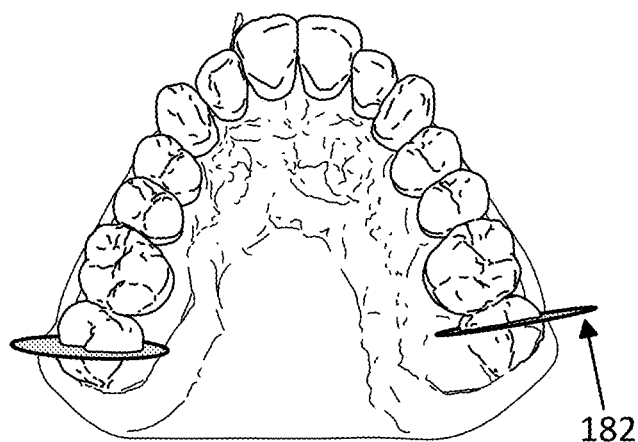
Figure 5D:
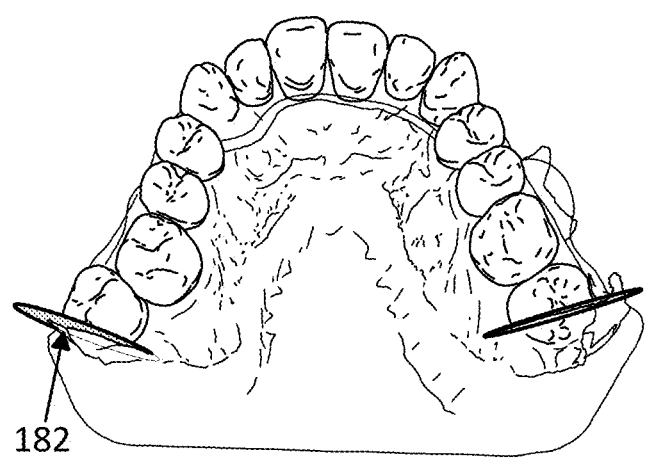
Figure 5E:
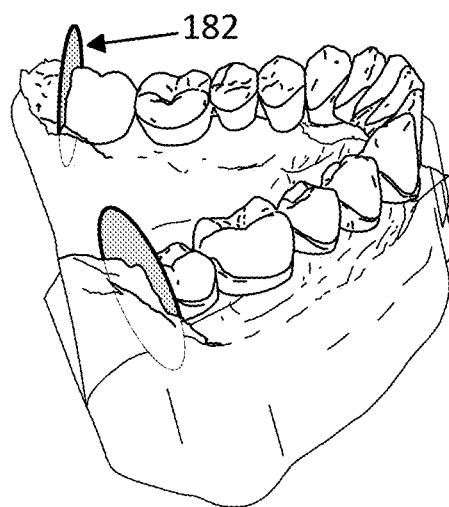

The trim plane engine can further implement one or more automated agents to adjust the trim plane normal vector angulation. In one embodiment, referring to FIG. 4E, the trim plane engine can find the angle α between the tooth z-axis and the direction from the tooth center to the adjacent mesial tooth center. If this angle is less than $\pi/2$, the trim plane engine can be configured to rotate the normal vector by $\pi/2-\alpha$.

The scan trimming engine 177 may implement one or more automated agents configured to modify the 3D tooth model by trimming the tooth or teeth identified by the machine learning engine 175. For example, the 3D tooth model may be trimmed along the trim plane(s) identified by trim plane engine 176. In some implementations, only a portion of the tooth or teeth that requires trimming is trimmed by the scan trimming engine. For example, only the portion of the tooth or teeth that have missing or incomplete data may be trimmed or removed from the 3D tooth model (e.g., the portion of a tooth that is unerupted or covered in gingiva). This may be, for example, approximately ⅓ of the target tooth that is trimmed, ½ of the target tooth that is trimmed, ⅔ of the target tooth that is trimmed, etc.

FIGS. 5A-5E illustrate examples of a tooth (e.g., a molar) that requires trimming as identified by the machine learning engine 175. For example, the machine learning engine 175 may have determined that the tooth is partially covered in gingiva, is partially erupted, has missing scan data, or has distortions. The cutting line 182 for trimming is positioned along the trim plane as determined by the trim plane engine.

The trimming datastore 178 may be configured to store data relating to the probability that the 3D tooth model requires trimming from the machine learning engine 175 (e.g., the output from the machine learning engine) and the trim plane identified by trim plane engine 176. In some implementations, the trimming probability is a linear labeling score (e.g., a score ranging from 0.0 to 1.0, where 0.0 indicates a low probability that the 3D tooth model requires trimming and 1.0 indicates a high probability that the 3D tooth model requires trimming). Alternatively, the trimming probability can be a categorical output (e.g., "No Trim", "Most Likely No Trim", "Likely Not Trim", "Likely Trim", "Most Likely Trim", "Trim", etc.). The trimming datastore 178 may be further configured to store the location of the tooth or teeth that requires trimming. Additionally, the trimming datastore 178 may be configured to store the modified 3D tooth model or 3D model after trimming has been performed by the scan trimming engine 177.

Figure 6:
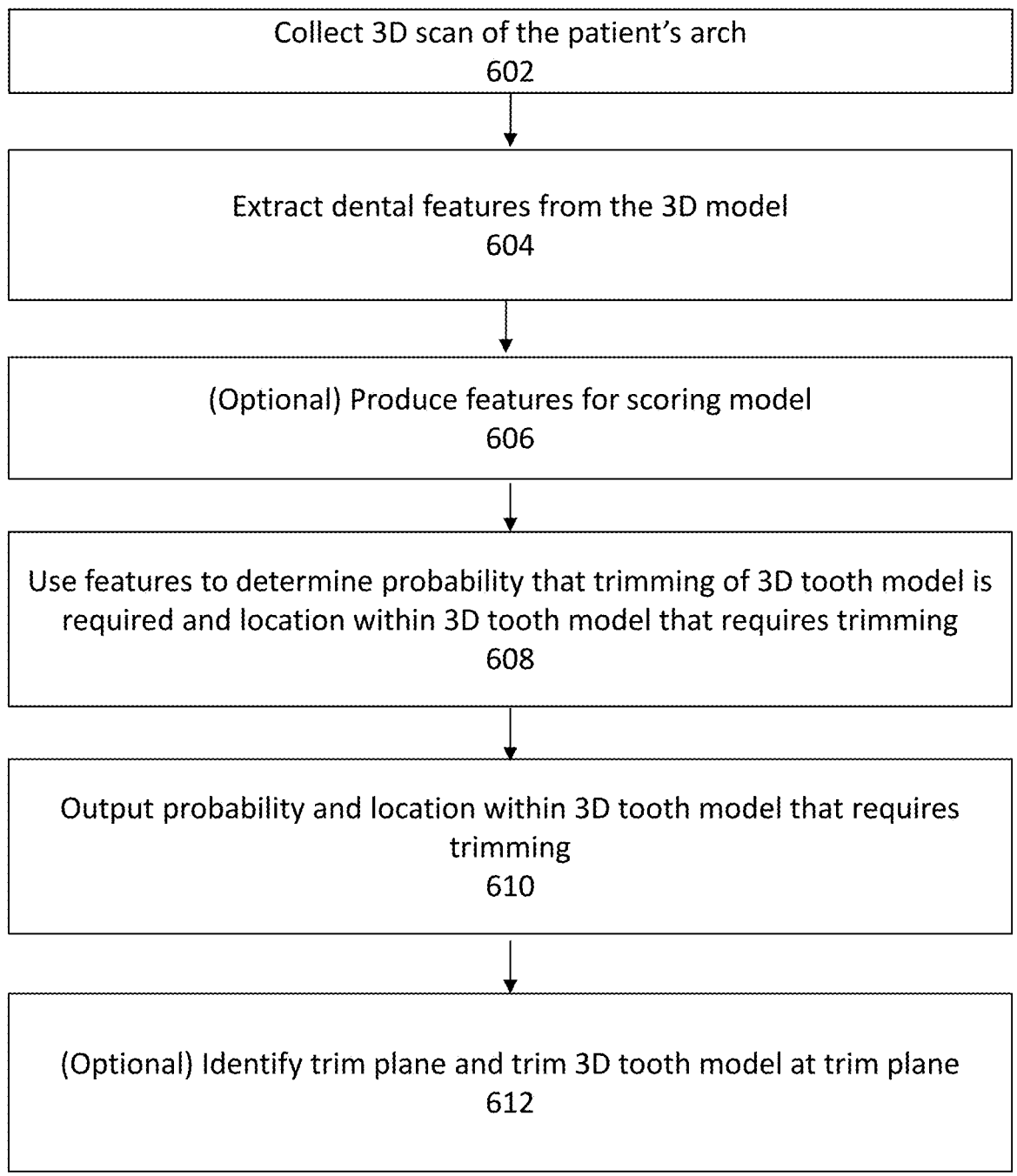
FIG. 6 is a flowchart describing one example of determining a post-treatment tooth position score.

FIG. 6 illustrates one example of a method for trimming missing or incomplete data from a 3D tooth model of a patient's dental arch. This method may be implemented by a system, such as one or more of the systems in the computing environment 100A, shown in FIG. 1A. At an operation 602, the system may collect a three-dimensional (3D) scan of the patient's dental arch. The 3D scan may be collected directly from the patient (e.g., using an intraoral scanner) or indirectly (e.g., by scanning a mold of the patient's dentition and/or be receiving a digital model of the patient taken by another, etc.).

The 3D scan may be prepared for further processing. For example, the 3D scan may be expressed as a digital mesh and/or segmented into individual teeth (and non-teeth elements, such as gingiva, arch, etc.). At an operation 604, raw dental features may be extracted from the 3D model of the patient's teeth (and in some variations from additional data about the patient or the patient's teeth or from prescription guidelines), e.g., using a feature extraction engine. For example, features from the individual tooth segmentation data may be extracted with the feature extraction engine. The tooth shape features may comprise, for example, the 3D point cloud, or alternatively, a subset of data points from the 3D point cloud specifically chosen to represent the shape, position, and orientation of the tooth.

At an optional operation 606, additional features for the scoring model may be produced. In one example, principal component analysis (PCA) can be implemented to obtain the dental features that will be used by the scoring model. In one implementation, the 3D dental mesh model of individual teeth comprises a scatter plot of points representing a patient's tooth, and PCA can be applied to the scatter plot to obtain vectors along the biggest distribution of scatter plots. In another example, automated feature exploration can be implemented (e.g., using deep neural networks or other feature selection methods) to produce the features for the scoring model.

At an operation 608, the extracted dental features and the produced features may be used exclusively or in combination with any other extracted feature described herein. The dental features may be provided to the classifier to determine the probability that the 3D tooth model requires trimming and to identify the location, tooth, or teeth within the 3D tooth model that requires trimming.

At an operation 610, the probability that the 3D tooth model requires trimming and the location, tooth, or teeth within the 3D tooth model that requires trimming may then be output. In some variations this information is used to modify a model (e.g., a 3D digital model) of the patient's teeth (e.g., dental arch). For example, at an optional operation 612, a trim plane can be identified when trimming is desirable. The trim plane may be identified from a parametric model representing an arch portion corresponding to the patient's teeth, as described above. In some implementations, the trim plane comprises a normal vector on at least one of the teeth as a tangent to the parametric model. The 3D tooth model may be trimmed at the trim plan to remove the missing or incomplete data identified by the machine learning algorithm.

Figure 7:
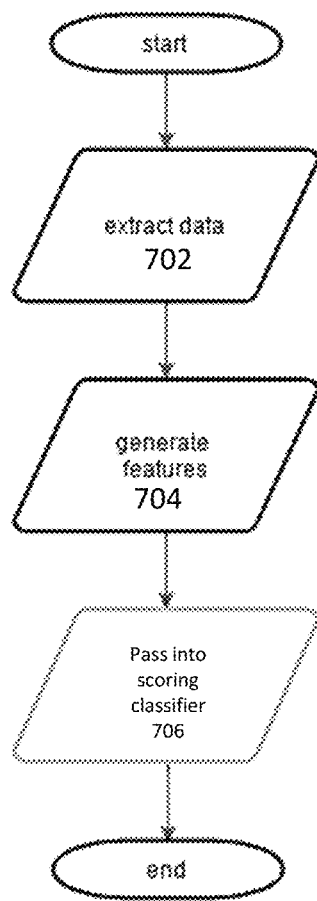
FIG. 7 is another flowchart describing one example of determining a post-treatment tooth position score.

FIG. 7 is another flowchart that shows the overall trimming system described above and describes a method of extracting and generating data to be passed into a tooth trimming system.

At an operation 702 of FIG. 7, data can be extracted for use by the trimming system. The data can include patient teeth data (e.g., 3D model/scanning of teeth) as well as clinical data about the patient (e.g., patient age, gender, prescription information, etc.). Next, at step 704 of FIG. 7, the detection system can generate features from the extracted data, including raw tooth features and produced features, as described above. Finally, at step 706 of FIG. 7, the features can be passed into the classifier to determine a probability that the 3D tooth model requires trimming and the location, tooth, or teeth within the 3D tooth model that requires trimming.

Figure 8:
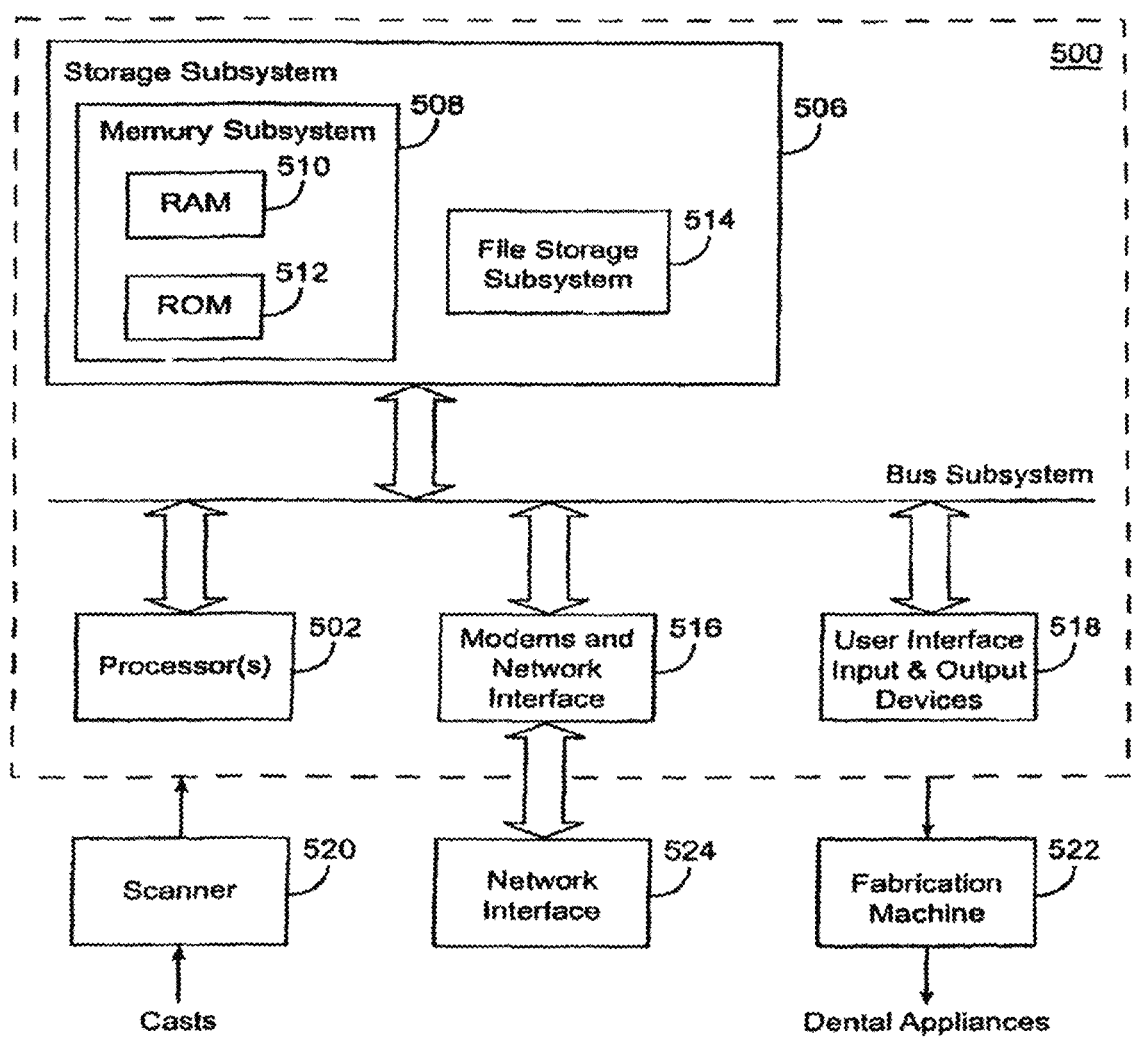
FIG. 8 is a simplified block diagram of a data processing system that may perform the methods described herein.

The methods described herein may be performed by an apparatus, such as a data processing system, which may include hardware, software, and/or firmware for performing many of these steps described above. For example, FIG. 8 is a simplified block diagram of a data processing system 500. Data processing system 500 typically includes at least one processor 502 which communicates with a number of peripheral devices over bus subsystem 504. These peripheral devices typically include a storage subsystem 506 (memory subsystem 508 and file storage subsystem 514), a set of user interface input and output devices 518, and an interface to outside networks 516, including the public switched telephone network. This interface is shown schematically as "Modems and Network Interface" block 516, and is coupled to corresponding interface devices in other data processing systems over communication network interface 524. Data processing system 500 may include a terminal or a low-end personal computer or a high-end personal computer, workstation or mainframe.

The user interface input devices typically include a keyboard and may further include a pointing device and a scanner. The pointing device may be an indirect pointing device such as a mouse, trackball, touchpad, or graphics tablet, or a direct pointing device such as a touchscreen incorporated into the display. Other types of user interface input devices, such as voice recognition systems, may be used.

User interface output devices may include a printer and a display subsystem, which includes a display controller and a display device coupled to the controller. The display device may be a cathode ray tube (CRT), a flat-panel device such as a liquid crystal display (LCD), or a projection device. The display subsystem may also provide nonvisual display such as audio output.

Storage subsystem 506 maintains the basic programming and data constructs that provide the functionality of the present invention. The software modules discussed above are typically stored in storage subsystem 506. Storage subsystem 506 typically comprises memory subsystem 508 and file storage subsystem 514.

Memory subsystem 508 typically includes a number of memories including a main random access memory (RAM) 510 for storage of instructions and data during program execution and a read only memory (ROM) 512 in which fixed instructions are stored. In the case of Macintosh-compatible personal computers the ROM would include portions of the operating system; in the case of IBMcompatible personal computers, this would include the BIOS (basic input/output system).

File storage subsystem 514 provides persistent (nonvolatile) storage for program and data files, and typically includes at least one hard disk drive and at least one floppy disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web.

In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected over various local-area or wide-area network media, including telephone lines. Similarly, the input devices and display need not be at the same location as the processor, although it is anticipated that the present invention will most often be implemented in the context of PCS and workstations.

Bus subsystem 504 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 520 is responsible for scanning casts of the patient's teeth obtained either from the patient or from an orthodontist and providing the scanned digital data set information to data processing system 500 for further processing. In a distributed environment, scanner 520 may be located at a remote location and communicate scanned digital data set information to data processing system 500 over network interface 524.

Fabrication machine 522 fabricates dental appliances based on intermediate and final data set information acquired from data processing system 500. In a distributed environment, fabrication machine 522 may be located at a remote location and acquire data set information from data processing system 500 over network interface 524.

Various alternatives, modifications, and equivalents may be used in lieu of the above components. Although the final position of the teeth may be determined using computer-aided techniques, a user may move the teeth into their final positions by independently manipulating one or more teeth while satisfying the constraints of the prescription.

Additionally, the techniques described here may be implemented in hardware or software, or a combination of the two. The techniques may be implemented in computer programs executing on programmable computers that each includes a processor, a storage medium readable by the processor (including volatile and nonvolatile memory and/or storage elements), and suitable input and output devices. Program code is applied to data entered using an input device to perform the functions described and to generate output information. The output information is applied to one or more output devices.

Each program can be implemented in a high level procedural or object-oriented programming language to operate in conjunction with a computer system. However, the programs can be implemented in assembly or machine language, if desired. In any case, the language may be a compiled or interpreted language.

Each such computer program can be stored on a storage medium or device (e.g., CD-ROM, hard disk or magnetic diskette) that is readable by a general or special purpose programmable computer for configuring and operating the computer when the storage medium or device is read by the computer to perform the procedures described. The system also may be implemented as a computer-readable storage medium, configured with a computer program, where the storage medium so configured causes a computer to operate in a specific and predefined manner.

Thus, any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the invention and that methods and structures within the scope of these claims and their equivalents be covered thereby.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and/or methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the patient matter may be practiced. As mentioned, other embodiments may be utilized and derived there from, such that structural and logical substitutions and changes may be made without departing from the scope of this disclosure. Such embodiments of the inventive patient matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method comprising:
   acquiring a three-dimensional (3D) model of a patient's teeth;

extracting one or more dental features of the patient's teeth from the 3D model of the patient's teeth, the one or more dental features corresponding to geometrical properties of the patient's teeth;

creating additional dental features by taking a principal component analysis (PCA) of the dental features of the patient's teeth;

applying the one or more dental features and the additional dental features to a classifier, the classifier configured to provide a probability the dental features and the additional dental features correspond to one or more trimming factors forming a basis to trim at least a portion of the 3D model of the patient's teeth; and outputting from a computing device the probability the dental features and the additional dental features correspond to the one or more trimming factors.

2. The method of claim 1, further comprising trimming the 3D model of the patient's teeth based on the probability the dental features and the additional dental features correspond to the one or more trimming factors.

3. The method of claim 1, further comprising trimming the 3D model of the patient's teeth based on the probability the dental features and the additional dental features correspond to the one or more trimming factors, wherein the trimming comprises trimming or removing at least one-third (⅓) of a target tooth from the 3D model of the patient's teeth.

4. The method of claim 1, wherein the probability the dental features and the additional dental features correspond to the one or more trimming factors corresponds to a location within the 3D model where trimming is desirable.

5. The method of claim 1, wherein the one or more dental features are extracted from a scan of the patient's teeth.

6. The method of claim 1, further comprising taking the 3D model of the patient's teeth.

7. The method of claim 1, further comprising acquiring the 3D model of the patient's teeth based on a scan from an intraoral scanner.

8. The method of claim 1, further comprising acquiring the 3D model of the patient's teeth based on a mold of the patient's teeth.

9. The method of claim 1, wherein the classifier implements one or more convolutional neural networks (CNNs) configured to classify the dental features.

10. A non-transitory computing device readable medium having instructions stored thereon, wherein the instructions are executable by a processor to cause a computing device to perform a method comprising:

acquire a three-dimensional (3D) model of a patient's teeth;

extract one or more dental features of the patient's teeth from the 3D model of the patient's teeth, the one or more dental features corresponding to geometrical properties of the patient's teeth;

create additional dental features by taking a principal component analysis (PCA) of the dental features of the patient's teeth;

apply the one or more dental features and the additional dental features to a classifier, the classifier configured to provide a probability the dental features and the additional dental features correspond to one or more trimming factors forming a basis to trim at least a portion of the 3D model of the patient's teeth; and output the probability the dental features and the additional dental features correspond to the one or more trimming factors.

11. The non-transitory computing device readable medium of claim 10, wherein the method comprises trimming the 3D model of the patient's teeth based on the probability the dental features and the engineered additional dental features correspond to the one or more trimming factors.

12. The non-transitory computing device readable medium of claim 11, wherein the method further comprises acquiring the 3D model from an intraoral scanner.

13. The non-transitory computing device readable medium of claim 10, wherein the method further comprises trimming the 3D model of the patient's teeth based on the probability the dental features and the additional dental features correspond to the one or more trimming factors, wherein the trimming comprises trimming at least one-third (⅓) of a target tooth from the 3D model of the patient's teeth.

14. The non-transitory computing device readable medium of claim 10, wherein the probability the dental features and the additional dental features correspond to the one or more trimming factors corresponds to a location within the 3D model where trimming is desirable.

15. The non-transitory computing device readable medium of claim 10, wherein the one or more dental features are extracted from a scan of the patient's teeth.

16. A method comprising:

acquiring a three-dimensional (3D) model of a patient's teeth;

extracting one or more dental features of the patient's teeth from the 3D model of the patient's teeth, the one or more dental features corresponding to geometrical properties of the patient's teeth;

applying the one or more dental features to a classifier, the classifier configured to provide a probability the dental features correspond to one or more trimming factors forming a basis to trim at least a portion of the 3D model of the patient's teeth; and outputting from a computing device the probability the dental features correspond to the one or more trimming factors; and trimming the 3D model of the patient's teeth based on the probability the dental features correspond to the one or more trimming factors, wherein the trimming comprises trimming or removing at least one-third (⅓) of a target tooth from the 3D model of the patient's teeth.

17. The method of claim 16, further comprising creating additional features by taking a principal component analysis (PCA) of the dental features of the patient's teeth.

18. The method of claim 16, wherein the classifier implements one or more convolutional neural networks (CNNs) configured to classify the dental features.

* * * * *